(12) United States Patent
Cunkle et al.

(10) Patent No.: US 6,218,536 B1
(45) Date of Patent: *Apr. 17, 2001

(54) 1,2-BIS-ADDUCTS OF STABLE NITROXIDES WITH SUBSTITUTED ETHYLENES AND STABILIZED COMPOSITIONS

(75) Inventors: Glen Thomas Cunkle, Stamford, CT (US); Thomas F. Thompson, Highland Mills, NY (US); Volker H. von Ahn, Mahopac, NY (US); Roland A. E. Winter, Armonk, NY (US)

(73) Assignee: Ciba Specialty Chemcials Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/168,056

(22) Filed: Oct. 7, 1998

Related U.S. Application Data

(63) Continuation-in-part of application No. 08/755,882, filed on Dec. 2, 1996, now Pat. No. 5,844,025.

(51) Int. Cl.$^7$ ............... C07C 239/20; C07D 211/94; C07D 295/22; C08K 5/3435
(52) U.S. Cl. ............... 540/596; 560/222; 560/231; 560/250; 560/251; 560/264; 560/129; 562/553; 562/567; 548/455; 548/461; 548/462; 548/519; 548/520; 548/523; 548/542; 526/204; 546/187; 546/189; 546/190; 546/191; 524/87; 524/98; 524/99; 524/102; 524/103; 524/104; 524/105; 564/300; 564/301; 558/458
(58) Field of Search ............... 526/204; 546/191, 546/187, 189, 190; 524/87, 98, 99, 102, 103, 104, 105; 564/300, 301; 558/458; 560/250, 251, 222, 264, 231, 129; 562/553, 567; 540/596; 548/523, 519, 520, 542, 455; 461/462

(56) References Cited

U.S. PATENT DOCUMENTS 5,322,960 * 6/1994 Sakamoto et al. .................. 560/205

FOREIGN PATENT DOCUMENTS 0309402A 3/1989 (EP) .

OTHER PUBLICATIONS

Journal of Flourine Chemistry 69(1994) 163–169 A. E. Tipping, et al.

J. Chemical Society C, 901 (1966)–R.E. Banks, et al.

J. Chemical Society C, 2777(1971)–R.E. Banks, et al.

Polymer Bulletin 6, 589 (1982) G. Moad, et al.

Journal of Organic Chemistry–D.W. Dixon, et al "Oxidation of 1,2–bis (hydroxylamines)" (1982) .

R.E. Banks, et al. Nitroxide Chemistry Part V. (1982).

T. J. Connolly, et al., Tetrahedron Letters, vol. 38, No. 17 (Feb. 17, 1997) pp. 1133–1136.

* cited by examiner

*Primary Examiner*—Frederick Krass
(74) *Attorney, Agent, or Firm*—Luther A. R. Hall

(57) ABSTRACT

1,2-Bis-adducts of stable hindered nitroxide compounds with substituted ethylenes are prepared by reacting two equivalents of nitroxyl compound with an ethylenically unsaturated compound such as styrene or an acrylate ester. These adducts are very effective inhibitors to prevent the premature polymerization of ethylenically unsaturated monomers when such monomers are distilled, processed or stored.

9 Claims, No Drawings

1,2-BIS-ADDUCTS OF STABLE NITROXIDES WITH SUBSTITUTED ETHYLENES AND STABILIZED COMPOSITIONS

This is a continuation-in-part of application Ser. No. 08/755,882, filed on Dec. 2, 1996, now U.S. Pat. No. 5,844,025, issued on Dec. 1, 1998.

The instant invention pertains to novel 1,2-adducts of stable hindered nitroxyl compounds with substituted ethylenes such as found in ethylenically unsaturated monomers. The adducts are very effective inhibitors for preventing the premature polymerization of vinyl monomers.

BACKGROUND OF THE INVENTION

Many of the industrially important ethylenically unsaturated monomers are highly susceptible to unwanted radical polymerization initiated either thermally or by adventitious impurities. Some examples of these monomers are styrene, acrylic and methacrylic acid, acrylate and methacrylate esters and acrylonitrile. Premature polymerization may occur during manufacture, purification or storage of the monomer. Many of these monomers are purified by distillation. It is in this operation where premature polymerization is most likely to occur and to be the most troublesome. Methods to prevent or reduce the amount of such polymerization are thus highly desirable since the prevention or mitigation of such premature polymerization increases the yield of purified monomer and also insures against costly and potentially dangerous runaway polymerization in the plant.

Stable hindered organic nitroxyl compounds included in this invention are those nitroxides which are fully substituted at the alpha carbon atoms. See L. B. Volodarsky et al., Synthetic Chemistry of Stable Nitroxides, CRC Press, Boca Raton, Fla., 1994. Bis-tri-fluoromethylnitroxide is a stable nitroxide and its 1,2-bis-adducts with ethylenes are known. See A. E. Tipping et al., J. Fluor. Chem., 69, 163 (1994); R. E. Banks et al., J. Chem. Soc. C, 901 (1966); and R. E. Banks et al., J. Chem. Soc., C, 2777 (1971).

1-Phenyl-1,2-bis(2,2,6,6-tetramethylpiperidin-1-yloxy)-ethane and 1-phenyl-1,2-bis(1,1,3,3-tetramethylisoindolin-2-yloxy)ethane are known bis-adducts as taught by G. Moad et al., Polymer Bull. 6, 589 (1982) who reported these materials as prepared by the reaction of 1-oxyl-2,2,6,6-tetramethylpiperidine and 2-oxyl-1,1,3,3-tetramethylisoindoline with styrene. No chemical Abstract Number was ever assigned to this first compound nor was any utility ever ascribed to such compounds.

T. J. Connolly et al., Tetrahedron Letters, 38, 1133 (1997) in a recently issued paper issued note that TEMPO (1-oxyl-2,2,6,6-tetramethylpiperidine) reacts with styrene and polystyrene to mediate autopolymerization and effect the polydispersity of polystyrene in "living" polymer systems.

OBJECTS OF THE INVENTION

One object of this invention is to provide novel bis-adduct compounds formed by the reaction of stable hindered organic nitroxyl compounds with an ethylenically unsaturated monomer.

Another object of this invention is to demonstrate the ability of these bis-adducts to prevent or mitigate the premature polymerization of ethylenically unsaturated monomers during distillation and purification.

Still another object of this invention is to provide compounds which exhibit effective stabilization efficacy to organic substrates subject to thermal or light induced radiation.

DETAILED DISCLOSURE

The instant invention pertains to novel 1,2-bis-adducts of formula I or II

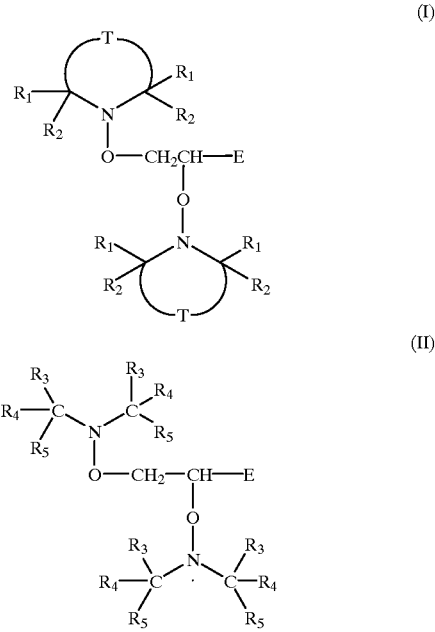

where $R_1$ and $R_2$ are independently alkyl of 1 to 4 carbon atoms, or $R_1$ and $R_2$ together are pentamethylene, preferably $R_1$ and $R_2$ are each methyl;

E is aryl of 6 to 10 carbon atoms, or said aryl substituted by alkyl of 1 to 4 carbon atoms or by halogen, or E is —COOH or —COOR$_6$ where $R_6$ is alkyl of 1 to 18 carbon atoms or hydroxyalkyl of 2 to 8 carbon atoms, or E is —CN, preferably E is —COOH, —CN or —COOR$_6$ where $R_6$ is alkyl of 1 to 4 carbon atoms, most preferably butyl;

$R_3$, $R_4$ and $R_5$ are independently alkyl of 1 to 4 carbon atoms, preferably methyl; and T is a group needed to complete a 5-, 6- or 7-membered ring or an 1,1,3,3-tetramethylisoindoline moiety, said T group can also be substituted by hydroxyl, by oxo, by acetamido, by —OR$_8$ where $R_8$ is alkyl of 1 to 18 carbon atoms, or by —O—CO—R$_9$ where $R_9$ is alkyl of 1 to 17 carbon atoms or phenyl, preferably $R_9$ is alkyl of 1 to 11 carbon atoms or phenyl; and with the proviso that 1-phenyl-1,2-bis(2,2,6,6-tetramethylpiperidin-1-yloxy)-ethane and 1-phenyl-1,2-bis(1,1,3,3-tetramethylisoindolin-2-yloxy)-ethane are excluded.

Formula I represents adducts of cyclic 5-, 6- and 7-membered ring stable nitroxides. Formula II represents adducts of acyclic stable nitroxides.

Another aspect of the instant invention is the use of the bis-adducts of formulas I and II as effective inhibitors against the premature polymerization of ethylenically unsaturated monomers. The monomers are any having at least one carbon—carbon double bond capable of undergoing free radical induced polymerization. Such monomers are well-known in commerce and comprise a wide variety of structural types. Typical examples of such monomers are the dienes such as butadiene and isoprene; halogenated monomers such as vinyl chloride, chloroprene, vinylidene chloride, vinylidene fluoride and vinyl fluoride; unsaturated acids such as acrylic acid, methacrylic acid and crotonic acid; unsaturated esters such as the acrylates and methacrylates exemplified by butyl acrylate, methyl methacrylate, ethyl acrylate and methyl acrylate; unsaturated nitriles such as acrylonitrile and methacrylonitrile; unsaturated ethers such as methyl vinyl ether; and miscellaneous vinyl monomers such as the vinyl pyridines; and diethyl vinylphosphonate.

These adducts would also be of use with vinyl aromatic monomers such as styrene, α-methylstyrene, p-chlorostyrene or divinylbenzene, but Moad et al. appear to suggest this in their experimental work using styrene.

Preferably the monomer is acrylic acid, methacrylic acid, butyl acrylate, ethyl acrylate or acrylonitrile.

The monomer composition stabilized against premature polymerization comprises (a) an ethylenically unsaturated monomer, and (b) an effective stabilizing amount of a compound of formula I or II as described above;

with the proviso that the vinyl aromatic compounds are excluded.

The effective stabilizing amount of component (b) is 1 to 10000 ppm by weight based on the weight of monomer of component (a). Preferably, the amount of component (b) is 10 to 1000 ppm by weight based on the monomer of component (a).

The activated polymerization inhibitor mixtures can be introduced into the monomer to be protected by any conventional method. It may be added just upstream of the point of desired application by any suitable means. In addition, this mixture may be injected separately into the distillation train along with the incoming feed of monomer or through separate entry points providing efficient distribution of the activated inhibitor mixture. Since the inhibitor is gradually depleted during operation, it is generally necessary to maintain the appropriate amount of the activated inhibitor mixture in the distillation system by adding additional inhibitor during the course of the distillation process. Such addition may be carried out either on a continuous basis or by intermittently charging fresh inhibitor into the distillation system if the concentration of the inhibitor is to be maintained above the minimum required level.

The instant invention also pertains to a stabilized composition which comprises (a) an organic material subject to the deleterious effects of heat, oxygen or actinic radiation, and (b) an effective stabilizing amount of a compound of formula I or II as described above.

The organic material is preferably a polymer, especially a polyolefin, such as polypropylene or polyethylene, or a polymer, copolymer or polymer blend which contains in at least one polymer or polymer component significant ethylenic unsaturation. Examples of the latter are polymers selected from the group consisting of ABS, HIPS, emulsion SBR, PP/EPDM, PP/NBR, PP/NR, ABS/PC, ABS/nylon, ABS/PVC, ABS/polyester, ABS/SMA, ABS/polysulfone, ASA/PC, aceta/elastomer, polyester/elastomer, nylon/elastomer, PPO/NR, EPDM/NBR and EPDM/olefin.

The following examples are meant to illustrate the instant invention and are not to be construed to limit the scope of the instant invention in any manner whatsoever.

Example 1

1,2-Bis-adduct of 1-Oxyl-2,2,6,6-tetramethyl-4-benzoyloxypiperidine and Styrene

A deoxygenated solution of 10 g of 1-oxyl-2,2,6,6-tetramethyl-4-benzoyloxypiperidine in 120 mL of styrene is heated at 100° C. for 24 hours. The unreacted styrene is then removed under reduced pressure. The title compound is isolated from the residue by chromatography and purified by crystallization from hexane/ethyl acetate to give 5.3 g of adduct product, melting at 175–176° C.

Example 2

1,2-Bis-adduct of 1-Oxyl-2,2,6,6-tetramethyl-4-benzoyloxypiperidine and 4Chlorostyrene When following the procedure of Example 1, an equivalent amount of 4-chlorostyrene is substituted for styrene, the title compound is obtained after purification by chromatography as a white solid melting at 76–78° C.

Example 3

1,2-Bis-adduct of 1-Oxyl-2,2,6,6-tetramethyl-4-hydroxypiperidine and Styrene

When following the procedure of Example 1, an equivalent amount of 1-oxyl-2,2,6,6-tetramethyl-4-hydroxypiperidine is substituted for 1-oxyl-2,2,6,6-tetramethyl-4-benzoyloxypiperidine, the tide compound is obtained after purification by chromatography as a white solid melting at 104–108° C.

Example 4

1,2-Bis-adduct of 1-Oxyl-2,2,6,6-tetramethylpiperidine and Styrene

When following the procedure of Example 1, an equivalent amount of 1-oxyl-2,2,6,6-tetramethylpiperidine is substituted for 1-oxyl-2,2,6,6-tetramethyl-4-benzoyloxypiperidine, the title compound is obtained after purification by chromatography as a colorless oil. This is the bisadduct made by Moad, et al.

Example 5

1,2-Bis-adduct of 1-Oxyl-2,2,6,6-tetramethyl-4-oxopiperidine and Styrene

When following the procedure of Example 1, an equivalent amount of 1-oxyl-2,2,6,6-tetramethyl-4-oxopiperidine is substituted for 1-oxyl-2,2,6,6-tetramethyl-4-benzoyloxypiperidine, the tide compound is obtained after purification by chromatography as a colorless waxy solid.

Example 6

1,2-Bis-adduct of 2-Oxyl-1,1,3,3-tetramethylisoindoline and Styrene

When following the procedure of Example 1, an equivalent amount of 2-oxyl-1,1,3,3-tetramethylisoindoline is substituted for 1-oxyl-2,2,6,6tetramethyl-4-benzoyloxypiperidine, the title compound is obtained after purification by chromatography as a white solid melting at 138–139° C. This is the bisadduct made by Moad, et al.

Example 7

1,2-Bis-adduct of 1-Oxyl-2,2,6,6-tetramethyl-4-benzoyloxypiperidine and Butyl Acrylate A deoxygenated solution of 30 g of 1-oxyl-2,2,6,6-tetramethyl-4-benzoyloxypiperidine in 50 mL of butyl acrylate is heated at 130° C. for 22 hours. The unreacted butyl acrylate is then removed under reduced pressure. The title compound is isolated from the residue by chromatography to give 9.0 g of adduct product as a colorless oil.

Example 8

1,2-Bis-adduct of 1-Oxyl-2,2,6,6-tetramethyl-4-hydroxypiperidine and Butyl Acrylate When following the procedure of Example 7, an equivalent amount of 1-oxyl-2,2,6,6-tetramethyl-4-hydroxypiperidine is substituted for 1-oxyl-2,2,6,6-tetramethyl-4-benzoyloxypiperidine, the title compound is obtained after purification by chromatography as a white solid melting at 115–117° C.

Examples 9–15

Commercial grade styrene is freed of the tert-butylcatechol storage stabilizer by washing with 1N aqueous sodium hydroxide followed by distillation under reduced pressure.

A 300-mL three-necked flask equipped with a thermometer, condenser, rubber septum and magnetic stirrer bar is charged with 100 g of styrene (purified as described above) without any inhibitor (Example 9) or charged in separate experiments with 200 mg of various test compounds of this invention in Examples 10–15. An oxygen-free atmosphere is established by five consecutive evacuations and backfilling with nitrogen, followed by sparging the styrene solution with pure nitrogen for 15 minutes. The vessel is immersed into a mechanically stirred and thermostatically controlled oilbath at 120° C. Small aliquots are removed periodically and analyzed for polymer content. The amount of polystyrene formed is then determined by refractive index measurements, calibrated with authenic polystyrene in styrene solutions of known concentrations. The results are shown in the table below.

|  | Compound of | Percent Polymer Formed after Heating | | |
| --- | --- | --- | --- | --- |
| Example | Example | 30 minutes | 60 minutes | 90 minutes |
| 9 | none | 3.7 | 8.4 | — |
| 10 | 1 | 0.0 | 0.5 | 2.8 |
| 11 | 2 | 0.0 | 0.8 | 3.8 |
| 12 | 3 | 0.0 | 0.2 | 1.6 |
| 13 | 4 | 0.0 | 0.0 | 1.0 |
| 14 | 5 | 0.1 | 0.1 | 1.9 |
| 15 | 6 | 0.0 | 0.2 | 1.3 |

It is clear from these data that each of the instant adduct compounds of Examples 10–15 provide far superior inhibition efficacy to prevent or mitigate the premature polymerization of the styrene monomer compared to the uninhibited styrene sample of Example 9.

Example 16

1,2-Bis-adduct of 1-Oxyl-2,2,6,6-tetramethyl-4-acetamidopiperidine and Styrene

When following the procedure of Example 1, an equivalent amount of 1-oxyl-2,2,6,6-tetramethyl-4-acetamidopiperidine is substituted for 1-oxyl-2,2,6,6-tetramethyl-4-benzoyloxypiperidine, the title compound is obtained after purification by chromatography.

Example 17

Light Stabilization of ABS/Polycarbonate Blends

A 50/50 blend of ABS (containing a hindered amine stabilizer compound of formula I) and polycarbonate is prepared by compounding the mixed resin pellets in a mini Brabender extruder. Injection molded 125 mil (3.2 mm) Izod bars are then prepared for evaluation of light stability, under standard interior automotive Xenon Arc WeatherOmeter exposure and spray Xenon Arc WeatherOmeter exposure tests.

The ABS/Polycarbonate blend containing the instant stabilizer compound of formula I shows enhanced light stabilization compared to control polymer having no hindered amine compound present.

Example 18

Stabilization of Polypropylene Fiber

When a polypropylene fiber contains a stabilizer compound of formula I, it exhibits superior light and thermal stability compared to an unstabilized polypropylene fiber.

What is claimed is:

1. A compound of formula II

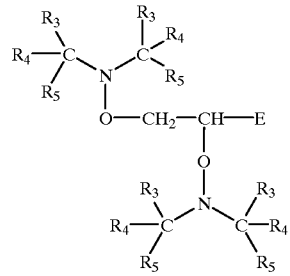

(II)

E is aryl of 6 to 10 carbon atoms, or said aryl substituted by alkyl of 1 to 4 carbon atoms or by halogen, or E is —COOH or —COOR$_6$ where R$_6$ is alkyl of 1 to 18 carbon atoms or hydroxyalkyl of 2 to 8 carbon atoms, or E is —CN, R$_3$, R$_4$ and R$_5$ are each methyl.

2. A compound according to claim 1 wherein E is —COOH, —CN or —COOR$_6$ where R$_6$ is alkyl of 1 to 4 carbon atoms.

3. A compound according to claim 2 wherein R$_6$ is butyl.

4. A composition stabilized against premature polymerization which comprises a. an ethylenically unsaturated monomer, and b. an effective stabilizing amount of a compound of formula I or II

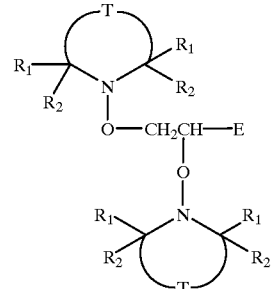

(I)

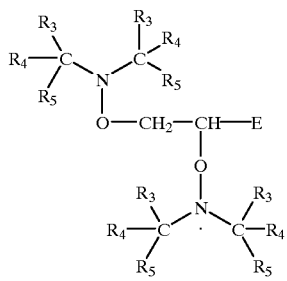

(II)

where $R_1$ and $R_2$ are independently alkyl of 1 to 4 carbon atoms, or $R_1$ and $R_2$ together are pentamethylene, E is aryl of 6 to 10 carbon atoms, or said aryl substituted by alkyl of 1 to 4 carbon atoms or by halogen, or E is —COOH or —COOR$_6$ where $R_6$ is alkyl of 1 to 18 carbon atoms or hydroxyalkyl of 2 to 8 carbon atoms, or E is —CN, $R_3$, $R_4$ and $R_5$ are independently alkyl of 1 to 4 carbon atoms, and T is a group needed to complete a 5-, 6- or 7-membered ring or an 1,1,3,3-tetramethylisoindoline moiety, where said T group is unsubstituted or substituted by hydroxyl, by oxo, by —OR$_8$ where $R_8$ is alkyl of 1 to 18 carbon atoms, or by —O—O—R$_9$ where $R_9$ is alkyl of 1 to 17 carbon atoms or phenyl;

with the proviso that vinyl aromatic monomers are excluded.

5. A composition according to claim 4 wherein the ethylenically unsaturated monomer is selected from the group consisting of dienes; halogenated vinyl monomers; unsaturated acids; unsaturated esters; unsaturated nitriles; unsaturated ethers; and diethyl vinylphosphonate.

6. A composition according to claim 5 wherein the monomer is butadiene, isoprene, vinyl chloride, chloroprene, vinylidene chloride, vinylidene fluoride, vinyl fluoride, acrylic acid, methacrylic acid, crotonic acid, butyl acrylate, methyl methacrylate, ethyl acrylate, methyl acrylate, acrylonitrile, methacrylonitrile or methyl vinyl ether.

7. A composition according to claim 6 wherein the monomer is acrylic acid, methacrylic acid, butyl acrylate, ethyl acrylate or acrylonitrile.

8. A composition according to claim 4 wherein the effective stabilizing amount of component (b) is 1 to 10000 ppm by weight based on the weight of monomer of component (a).

9. A composition according to claim 8 wherein the effective stabilizing amount of component (b) is 10 to 1000 ppm by wherein based on the monomer of component (a).

* * * * *